(12) United States Patent
Garin

(10) Patent No.: US 9,885,666 B2
(45) Date of Patent: Feb. 6, 2018

(54) OPTICAL INSPECTION STATION FOR DETECTING LIGHT-REFLECTING DEFECTS

(75) Inventor: Jean-Francois Garin, Lyons (FR)

(73) Assignee: TIAMA, Vourles (FR)

( * ) Notice: Subject to any disclaimer, the term of this patent is extended or adjusted under 35 U.S.C. 154(b) by 1975 days.

(21) Appl. No.: 12/312,032

(22) PCT Filed: Oct. 24, 2007

(86) PCT No.: PCT/FR2007/052239
§ 371 (c)(1),
(2), (4) Date: Feb. 4, 2010

(87) PCT Pub. No.: WO2008/050067
PCT Pub. Date: May 2, 2008

(65) Prior Publication Data
US 2010/0128120 A1 May 27, 2010

(30) Foreign Application Priority Data

Oct. 24, 2006 (FR) ...................................... 06 54490

(51) Int. Cl.
*H04N 9/47* (2006.01)
*G01N 21/90* (2006.01)
*G01N 21/88* (2006.01)

(52) U.S. Cl.
CPC ..... *G01N 21/9054* (2013.01); *G01N 21/8806* (2013.01)

(58) Field of Classification Search
CPC ....................... G01N 21/9054; G01N 21/8806

USPC ........................................................ 348/135
See application file for complete search history.

(56) References Cited

U.S. PATENT DOCUMENTS

| 5,661,294 | A | * | 8/1997 | Buchmann et al. ...... 250/223 B |
| 6,122,045 | A | * | 9/2000 | Pike et al. .................. 356/237.1 |
| 6,175,107 | B1 | * | 1/2001 | Juvinall ..................... 250/223 B |
| 6,211,952 | B1 | | 4/2001 | Weiland et al. |
| 7,148,961 | B1 | | 12/2006 | Ringlien |
| 7,289,646 | B2 | * | 10/2007 | Hirahara et al. ............... 382/110 |

FOREIGN PATENT DOCUMENTS

| EP | 0 060 918 | 9/1982 |
| EP | 0 456 910 | 11/1991 |
| EP | 0 483 966 | 5/1992 |
| EP | 1 147 405 | 10/2001 |

(Continued)

*Primary Examiner* — Richard Torrente
(74) *Attorney, Agent, or Firm* — Clark & Brody

(57) ABSTRACT

The invention relates to an optical inspection station comprising: an illumination system capable of delivering a series of light beams illuminating an inspection region of the object at various angles of incidence; a camera equipped with a lens for producing images of the inspection region during rotation of the object; and a unit for analyzing and processing the images taken by the camera so as to detect the presence of reflecting defects in the images. According to the invention, the optical inspection station includes a series of optical elements for deflecting, in the air, rays reflected by the inspection region, these being placed between the inspection region and the lens so as to form, in each image, a series of views of the inspection region taken at different angles of viewing.

11 Claims, 2 Drawing Sheets

(56) References Cited

FOREIGN PATENT DOCUMENTS

| | | |
|---|---|---|
| FR | 1445144 | 7/1966 |
| JP | 61-25041 | 2/1986 |
| JP | 2002-267611 | 9/2002 |

* cited by examiner

OPTICAL INSPECTION STATION FOR DETECTING LIGHT-REFLECTING DEFECTS

The present invention concerns the technical area of inspecting hollow, translucent or transparent objects or articles, such as bottles or jars, with a view to detecting any defects occurring in these objects and which have the characteristic of reflecting light.

The subject of the invention more particularly concerns the area relating to the inspection of objects driven in rotation with a view to detecting defects in the form of surface cracks, by making use of their essential characteristic i.e. that of reflecting incident light.

Defects of surface crack type are micro-cracks occurring within a material which may initiate the propagation of cracks possibly leading to destruction of the object when subject to heat shock for example or to mechanical impact. Surface cracks are generally either substantially vertical i.e. substantially paralleled to the axis of longitudinal symmetry of the object, or substantially horizontal i.e. extending along a plane substantially perpendicular to said axis of symmetry. Having regard to the fact that said defects are likely to affect the characteristics of the objects, and more seriously to be of real danger for users, the prior art has put forward numerous solutions for the detection of surface cracks.

Patent application EP 0 456 910 for example describes a device inspection for hollow articles intended to be placed in rotation about their longitudinal axis of symmetry. An illumination system is able to provide an incident light beam concentrated by a lens on the upper part of the ring of the object. A receiver system such as a matrix camera receives the light beam reflected by vertical surface cracks in particular when the article is rotated. The camera is linked to a processing unit indicating whether the reflected beams exceed a pre-determined light intensity threshold over and above which a defect is ascertained.

Patent application EP 0 483 966 proposes using a device comprising a light source illuminating the bottom part of a bottle placed on a holder driven in rotation. A camera takes images of the bottom of the bottle through a scanning window arranged in the bottle holder. The camera is linked to a unit analysing and processing the received light beams, that is adapted to form successive images of the bottle at a given speed, each of the images being formed of a determined number of pixels. The analysis and processing unit, after re-synchronizing two successive images, then calculates the difference between the pixels of the two said images and makes a comparison with respect to threshold values so that a distinction can be made between reflected beams of stationary type, corresponding to parasite reflection, from those of variable type corresponding to defects in the object.

Patent EP 1 147 405 describes a bottle inspection device comprising at least five camera heads chosen from among the group consisting of endoscope end cameras and image sensors distanced from an image processing device. Said device therefore sets out to multiply the camera heads so as to increase the number of images taken as the bottle is rotated. Said device provides a particularly costly solution having regard to the high number of camera heads. Also, in principle it proves to be difficult to install as many sensors on a machine manufacturing glass objects.

In the technical area of optical bottle inspection, it is also known to use optical elements of Fresnel lens type (JP 61 025 041), cylindrical mirror type (JP 2002 267 611) or tubular mirror type (EP 0 060 918) to observe several portions of the object simultaneously from one same viewing position. Said systems are not adapted for efficient, reliable detection of surface cracks.

The present invention therefore sets out to overcome the disadvantages of the prior art by proposing an optical inspection station to detect light-reflecting defects occurring in a hollow transparent or translucent object driven in rotation, said station being able to detect surface cracks efficiently and reliably whilst limiting the number of cameras installed.

To achieve this objective, the optical inspection station according to the invention detects light-reflecting defects occurring in a hollow transparent or translucent object driven in rotation about its axis of symmetry, the inspection station comprising:
  a lighting system able to supply a series of light beams illuminating an inspection area of the object at different angles of incidence,
  a camera equipped with a lens producing images of the inspection area during rotation of the object,
  and an analysis and processing unit of the images taken by the camera to detect the present of reflective defects in the images.

According to the invention, the optical inspection station comprises a series of optical elements deflecting into air the rays reflected by the inspection area, arranged between the inspection area and the lens, so as to form a series of views of the inspection area in each image, these views taken at different viewing angles.

According to one example of embodiment, the optical deflection elements are arranged either side of the optical viewing axis of the camera.

Advantageously, the optical deflection elements are arranged symmetrically relative to the optical viewing axis of the camera.

If several optical deflection elements are arranged on the same side of the optical viewing axis of the camera, these optical deflection elements have angles of optical deflection that differ from each other.

For example the optical deflection elements consist of spherical lenses, cylindrical lenses, prisms or mirrors.

According to one preferred variant of embodiment, the optical deflection elements consist of Fresnel prisms or Fresnel lenses.

For example, the light system and the optical deflection elements are arranged on the same side with respect to the object.

According to one first application, the optical inspection station comprises optical deflection elements arranged side by side in a horizontal direction in order to detect vertical surface cracks.

According to another example of embodiment, the lighting system and the optical deflection elements are arranged either side of the object.

According to another application, the optical inspection station comprises optical deflection elements that are superimposed in a vertical direction in order to detect horizontal surface cracks.

Evidently, it could be envisaged that the optical inspection station comprises both optical deflection elements arranged side by side in a horizontal direction to detect vertical surface cracks, and optical deflection elements that are superimposed in a vertical direction in order to detect horizontal surface cracks. According to this example, the optical inspection station comprises a camera associated with a lens adapted to detect horizontal surface cracks and vertical surface cracks.

According to one advantageous characteristic, the image analysis and processing unit ensures a comparison between the data extracted from the views of the images taken so as to distinguish reflected beams of stationary type from those of mobile type corresponding to defects in the object.

A further object of the invention is to propose an inspection installation comprising means to place the objects in rotation, equipped with at least one inspection station conforming to the invention.

Various other characteristics will become apparent from the description given below with reference to the appended drawings which, as non-limiting examples, illustrate forms of embodiment of the subject of the invention.

Figure 1:
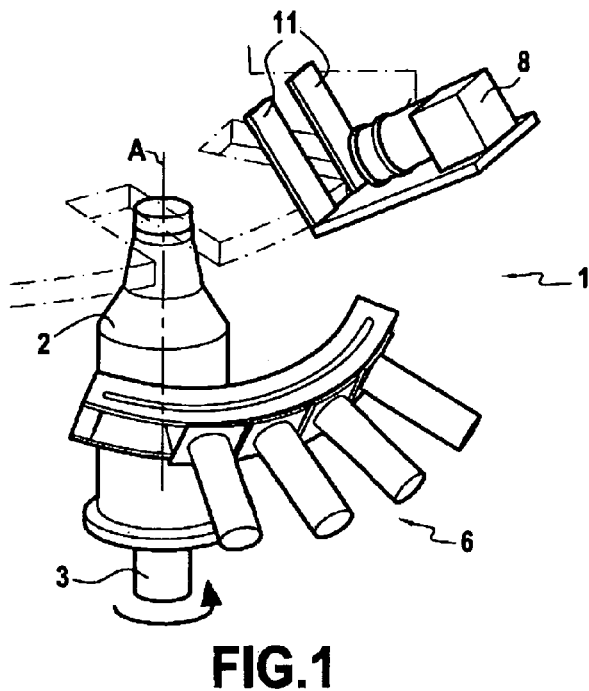
FIG. 1 is a perspective diagram showing a first example of embodiment of an optical inspection station conforming to the invention.
Figure 2:
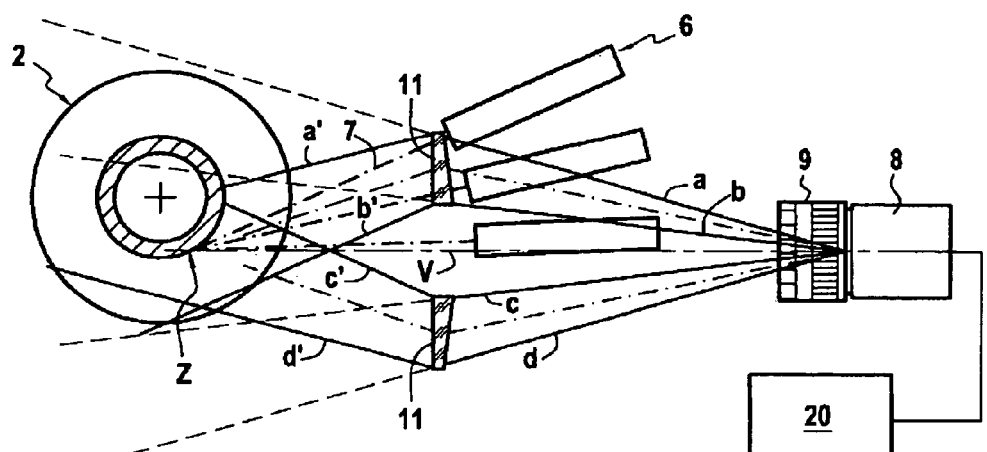
FIG. 2 is an overhead view of the inspection station illustrated FIG. 1.

With respect to FIGS. 1 and 2, the subject of the invention concerns an optical inspection station 1 to detect light-reflecting defects occurring in hollow, transparent or translucent objects 2. For example, the objects 2 are bottles, jars or flasks having a longitudinal axis of symmetry A and made in glass or a plastic material. The optical inspection station 1 is intended to be installed on a production line of the objects 2 with a view to detecting any defects in the walls of these objects. As defects, the optical inspection station 1 is able to detect surface cracks which may occur in a predetermined inspection area Z. As is conventional, the objects 2 are taken in charge by a suitable handling system 3 ensuring the rotation of the objects 2 about their axis of symmetry A.

The inspection station 1 comprises a lighting system 6 able to provide a series of light beams 7 illuminating the inspection area Z of the object from different incident angles. It is to be appreciated that the inspection area Z corresponds to a limited surface of the object which, in the illustrated example, corresponds to part of the ring of the object. For example, the lighting system 6 comprises several light sources such as light-emitting diodes or another light source associated with optical fibres for example and/or lenses. This lighting system 6 is adapted to illuminate the inspection area Z at different angles of incidence. Rotation of the object 2 on a lathe about the axis of symmetry A allows the entire periphery of the object to be inspected, namely the ring in the example under consideration.

The optical inspection station 1 comprises a camera 8 equipped with a lens 9 taking images of the inspection area Z as the object 2 is rotated. The camera 8 is a matrix camera for example.

According to the invention, the optical inspection station 1 comprises a series of optical deflection elements 11 deflecting into air the rays deflected by the inspection area Z. These optical deflection elements 11 are arranged between the inspection area Z and the lens 9 so as to form an image I of the inspection area Z, this image I comprising a series of views of this area taken at different viewing angles. These optical deflection elements 11 are positioned so as to deflect the light rays into air in the direction of the lens 9. These optical deflection objects 11 can consist of spherical lenses, cylindrical lenses, prisms or mirrors.

According to one preferred characteristic of embodiment, the optical deflection elements 11 are Fresnel lenses or Fresnel prisms.

In the example of embodiment shown FIGS. 1 and 2, the optical deflection elements 11 consist of prisms totaling two in number. In this example, the optical deflection elements 11 are arranged either side of the optical viewing axis V of the camera 8. According to one preferred characteristic of embodiment, the optical deflection elements 11 are arranged symmetrically relative to the optical viewing axis V of the camera.

Figure 3:
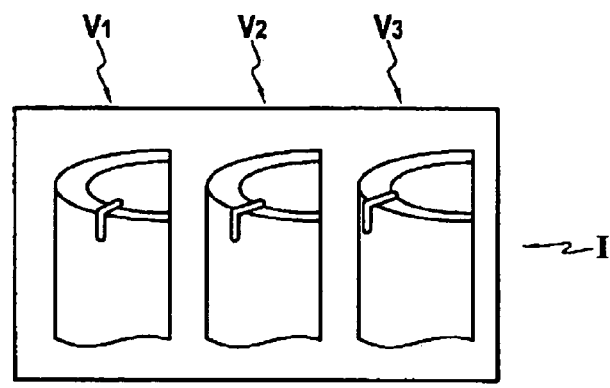
FIG. 3 illustrates an example of an image taken by an optical inspection station conforming to the invention.

As can be clearly seen in the example illustrated FIGS. 2 and 3, the optical deflection elements 11 are arranged so as to form an image I with three views $V_1$, $V_2$, $V_3$ of the inspection area Z. The field angle a-d of the lens 9 and camera 8 is divided into different areas, namely three areas in the example. Each area corresponds to a view of the object taken from a different angle. The inspection area Z is therefore observed under three different directions of observation i.e.:

a-b; a'b' on whose pathway, an optical deflection element 11 is placed allowing a view $V_1$ to be formed, c-d; c'-d' on whose pathway, an optical deflection element 11 is placed allowing a view $V_3$ to be formed, b-c left free by the optical deflection elements 11 about the viewing axis V allowing the camera to maintain a direct view, to form view $V_2$.

It is to be considered that each optical deflection element 11 allows the inspection area Z to be imaged from a different viewing angle, for the purpose of forming views $V_1$, $V_2$, whilst the viewing angle of the camera allows a view $V_3$ to be taken of the inspection area Z so that an image I can be obtained consisting of three views $V_1$, $V_2$, $V_3$ of the inspection area Z taken from three different viewing angles.

With said arrangement, it is possible to increase the probability of recovering the light emitted by a light-reflecting defect, by observing the inspection area from different viewing angles.

In the illustrated example, the optical deflection elements 11 consist of two prisms. It is to be noted that these prisms can be replaced by Fresnel lenses or mirrors. In this last example of embodiment, the camera is arranged on the other side of the object to recover the light rays. Similarly, in the illustrated example, the two optical deflection elements 11 leave a field of observation subsisting between them for the camera. It may be contemplated to divide the field a-d into two adjacent observation areas through the optical deflection elements 11 placed side by side so as to obtain an image I with only two views $V_1$ and $V_3$.

Evidently, it can be considered to use a higher number of optical deflection elements. For example, provision may be made to arrange four optical deflection elements 11 mounted symmetrically relative to the optical viewing axis V of the camera. In this case, the two optical deflection elements 11 arranged on one same side of the optical viewing axis V have different optical deflection angles. According to this variant, each image I taken comprises five views of the inspection area Z taken from five different viewing angles.

The camera 8 is linked to a unit 20 analysing and processing images taken as the object is rotated. It is to be considered that during the rotation of the object on the lathe, the camera 8 takes a succession of images I each comprising a series of views of the inspection area Z taken from different viewing axes. This unit 20 ensures a comparison between the data extracted from the views of the images taken successively so as to distinguish between reflected beams of stationary type and reflected beams of mobile type corresponding to defects in the object.

In the example illustrated FIGS. 1 and 2, the optical deflection elements 11 and the lighting system 6 are arranged on the same side with respect to the object 2. Also, the optical deflection elements 11 are positioned side by side in a horizontal direction for advantageous detection of vertical surface cracks. Further, provision may be made to equip an inspection installation of the objects with one or more inspection stations 1 conforming to the invention. It is to be noted that it may be considered to use two optical inspection stations 1 to inspect two inspection areas Z located diametrically opposite on the object 2.

Figure 4:
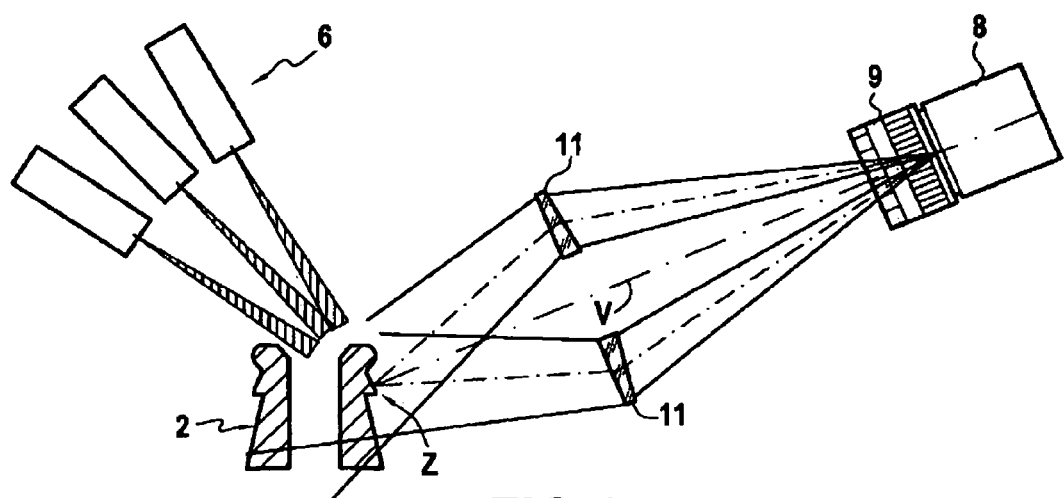
FIG. 4 is a view of another exemplary embodiment of an optical inspection station for the detection of horizontal surface cracks.

FIG. 4 illustrates another variant of embodiment of the inspection station 1 more precisely adapted to detect horizontal surface cracks. According to this variant of embodiment, the lighting system 6 and the optical deflection elements 11 are arranged either side of the object 2. In addition, the optical deflection elements 11 are superimposed in a substantially vertical direction. According to this variant, the optical deflection elements 11 are tilted at an angle of 90° relative to the optical deflection elements 11 illustrated FIG. 1.

Evidently, it may be considered to produce an inspection station 1 that is adapted to detect both horizontal surface cracks and vertical surface cracks. In this respect, the inspection station 1 comprises optical deflection elements 11 arranged side by side in a horizontal direction to detect vertical surface cracks, and optical deflection elements 11 that are superimposed in a vertical direction to detect horizontal surface cracks. The field angle of the lens and camera is therefore divided into at least as many areas as there are optical deflection elements 11 inserted on the pathway of the reflected light.

The invention is not limited to the described, illustrated examples since various modifications may be made thereto without departing from the scope of the invention.

The invention claimed is:

1. An optical inspection station to detect light-reflecting defects shown by a transparent or translucent hollow object driven in rotation about its axis of symmetry, the inspection station comprising:
    a lighting system able to supply a series of light beams illuminating one inspection area of the object at different angles of incidence,
    a camera equipped with a lens producing images of the inspection area during rotation of the object, the lens having a field angle,
    characterized in that the optical inspection station comprises a series of optical elements deflecting into air in a direction of the lens rays reflected by the one inspection area arranged between the one inspection area and the lens so as to divide the field angle of the lens into different areas, each area corresponding to a view of the one inspection area taken from different viewing angles, so as to form an image of the one inspection area, said image comprising a series of views of the one inspection area taken at different viewing angles, and wherein the optical elements are superimposed in a vertical direction to detect horizontal surface cracks.

2. The optical inspection station according to claim 1, characterized in that the optical deflection elements are arranged on either side of the optical viewing axis of the camera.

3. Optical inspection station according to claim 1, characterized in that the optical deflection elements are arranged symmetrically relative to the optical viewing axis of the camera.

4. The optical inspection station according to claim 1, characterized in that the optical deflection elements arranged on one same side of the optical viewing axis of the camera have angles of optical deflection that differ from each other.

5. The optical inspection station according to claim 1, characterized in that the optical deflection elements consist of spherical lenses, cylindrical lenses, prisms or mirrors.

6. The optical inspection station according to claim 5, characterized in that the optical deflection elements consist of Fresnel prisms or Fresnel lenses.

7. The optical inspection station according to claim 1, characterized in that the lighting system and the optical deflection elements are arranged on the same side relative to the object.

8. The optical inspection station according to claim 1, characterized in that the optical inspection station comprises optical deflection elements arranged along a horizontal direction, to detect vertical surface cracks.

9. The optical inspection station according to claim 1, characterized in that the lighting system and the optical deflection elements are arranged on either side of the object.

10. The optical inspection station according to claim 1, characterized in that the image analysis and processing unit ensures a comparison between the data extracted from the views of the images taken so as to distinguish reflected beams of stationary type from those of mobile type corresponding to defects of the object.

11. An installation to inspect transparent or translucent hollow objects, comprising means to rotate the objects, characterized in that it comprises at least one inspection station conforming to claim 1.

* * * * *